United States Patent [19]

Zehner

[11] 4,076,949

[45] Feb. 28, 1978

[54] PROCESS FOR THE PREPARATION OF OXALATE ESTERS

[75] Inventor: Lee R. Zehner, Media, Pa.

[73] Assignee: Atlantic Richfield Company, Los Angeles, Calif.

[21] Appl. No.: 794,778

[22] Filed: May 9, 1977

Related U.S. Application Data

[63] Continuation-in-part of Ser. No. 685,833, May 13, 1976, abandoned.

[51] Int. Cl.² .............................................. C07C 69/36
[52] U.S. Cl. ................................. 560/204; 260/465.4; 560/193; 560/196; 560/197; 560/198
[58] Field of Search ............... 560/204, 193, 196, 197, 560/198; 260/465.4

[56] References Cited

U.S. PATENT DOCUMENTS 3,393,136  7/1968  Fenton et al. ................... 260/485 R

FOREIGN PATENT DOCUMENTS 2,213,435  10/1923  Germany.
2,601,139  7/1976  Germany.
2,514,685  10/1975  Germany.

OTHER PUBLICATIONS

Fenton, et al., J. Org. Chem., 39 (5), pp. 701-704, (1974).

*Primary Examiner*—Jane S. Myers
*Attorney, Agent, or Firm*—Delbert E. McCaslin

[57] ABSTRACT

A process for the preparation of oxalate esters by reacting an alcohol with a mixture of carbon monoxide and oxygen in the presence of a catalytic mixture of:
  (a) a palladium, rhodium, platinum, copper, or cadmium metal salt compound or mixture thereof,
  (b) an aliphatic, cycloaliphatic, aromatic or heterocyclic amine or ammonia,
  (c) a copper (I), copper (II), iron (II) or iron (III) oxidant salt compound, and
  (d) an ammonium or substituted ammonium salt compound or acid with a counterion other than a halide.

Alternatively a ligand or coordination complex compound of the metal salt compound may be employed.

34 Claims, No Drawings

PROCESS FOR THE PREPARATION OF OXALATE ESTERS

CROSS REFERENCE TO RELATED APPLICATIONS

This application is a continuation-in-part application of application Ser. No. 685,833, filed May 13, 1976 now abandoned, entitled PROCESS FOR THE PREPARATION OF OXALATE ESTERS.

BACKGROUND OF THE INVENTION

A number of prior art processes have been proposed for the preparation of oxalate esters by the oxidative carbonylation of alcohols in the presence of metal salt catalysts, dehydrating agents and ferric or cupric redox agents in solution.

The present invention is directed to an improved process for the preparation of oxalate esters in high yield and avoiding problems associated with the prior art processes of carbonylating alcohols. More particularly, the present process relates to the synthesis of oxalates by reacting carbon monoxide, an alcohol, and oxygen under elevated temperature and pressure conditions in the presence of a catalytic mixture of materials comprising (1) a palladium, platinum, cadmium, rhodium, or copper salt compound, (2) at least a catalytic amount of an amine base, (3) a copper (I), copper (II), iron (II) or iron (III) oxidant salt in catalytic quantities and (4) catalytic amounts of an ammonium or substituted ammonium salt compound. Ligands or a coordination complex of the metal salt compounds may also be employed.

U.S. Pat. No. 3,393,136 describes a process for the preparation of oxalates by contacting carbon monoxide at superatmospheric pressure, with a saturated monohydric alcohol solution of a platinum group metal salt and a soluble ferric or cupric salt (redox agent) while maintaining the salts in a highly oxidized state by the simultaneous introduction of oxygen or the application of a direct current electrical potential to the reaction zone. Water scavengers or dehydrating agents such as alkyl orthoformic acid esters must be added to the liquid phase to prevent the accumulation of water.

In a recent article by Donald M. Fenton and Paul J. Steinwand, Journal of Organic Chemistry, Vol. 39, No. 5, 1974, pp. 701–704, a general mechanism for the oxidative carbonylation of alcohols to yield dialkyl oxalates using a palladium redox system, oxygen and dehydrating agents has been proposed. In the absence of the necessary dehydrating agent, a large amount of carbon dioxide is formed and oxalates are not produced. The necessity of the iron or copper redox system during the oxalate synthesis is emphasized.

A recent West German Pat. No. 2,213,435 discloses a method for the synthesis of oxalic acid and oxalate esters using water and alcohol respectively. A platinum group metal salt, a salt of a metal more electropositive than the platinum group metal, e.g. copper (II) chloride and an alkali metal salt such as lithium chloride comprise the catalyst. Oxygen in stoichiometric amounts was employed as the oxidant. A disadvantage of such reaction is that explosive mixtures of oxygen and carbon monoxide are necessary to effect reaction. Alcohol conversions of less than 5 percent are obtained. Under non-explosive conditions only trace amounts of oxalate can be obtained.

U.S. Pat. No. 3,994,960 describes a process for the production of dialkyl oxalates by reacting an aliphatic alcohol with CO and oxygen under pressure in the presence of a catalyst of a mixture of a salt of a metal from the platinum group and a salt of copper or iron and a reaction accelerator including nitrates, sulfates, bicarbonates, carbonates, tertiary amines and hydroxides and carboxylates of alkali metals and alkaline earth metals, pyridine, quinoline, urea and thiourea. Conversion of the alcohol employed to the dialkyl oxalates in such process is low, generally less than 9 mole percent.

In a process similar to that of U.S. Pat. No. 3,994,960 above, West German Offenlegungsschrift No. 2,601,139 shows the production of oxalic acid or its alkyl esters by reacting aliphatic alcohols or water with oxygen and carbon monoxide in the presence of palladium salts, redox salts and a base of amine or ammonia.

Many important commercial applications have been developed for the oxalate products of this invention, for example, cellulose ether or ester and resin solvents, as dye intermediates and the preparation of pharmaceuticals.

The process of the present invention provides an improved process for the oxidative carbonylation of an alcohol to produce an oxalate ester. Thus, there is provided a high conversion of the alcohol employed and excellent yield selectivity to the oxalate ester. Carbonate esters, carbon dioxide and alkyl formate as well as other side products commonly associated with such reactions are suppressed by employing as part of the catalyst the ammonium or substituted ammonium salt compound, i.e., the amine salt, in conjunction with the amine, and the palladium, rhodium, platinum, copper or cadmium metal salt compound and the copper (I), copper (II), iron (II) or iron (III) oxidant salt compound and alternatively a ligand or coordination complex, such as lithium iodide, and by initially charging the reactants in an anhydrous condition. The addition and presence of the amine salt in the catalytic mixture of the invention has been found to be necessary in order to achieve the increased selectivity and yield of oxalate ester not obtained by prior art processes. The addition of the amine salt maintains the proton acidity of the reaction system.

Other advantages of the present invention, as compared to known prior art processes for the production of oxalate esters are (1) elimination of the use of expensive water scavengers, by substantially inhibiting side reactions resulting from the formation of water in the reaction system, e.g., alkyloxalate anion (ROOC-COO—), oxalate dianion ($C_2O_4^=$), and carbonate anion ($CO_3^=$), (2) ease of recovery and reoxidation and recycle of reduced oxidant salts and regeneration and recycle of the metal salt compounds, (3) avoiding the use of large amounts of corrosive halogen ions and in some cases, elimination of halogen ion concentrations, (4) elimination of hazardous operational conditions by avoiding explosive mixtures of oxygen and carbon monoxide, (5) the ability to employ the more readily available copper, or cadmium salt compounds in place of the more expensive platinum group metals or metal salt compounds, and (6) the ability to employ ammonia, or a primary or secondary as well as a tertiary amine base.

SUMMARY OF THE INVENTION

According to the present invention there is provided a much improved catalytic oxidative carbonylation process for the preparation in high yield of oxalate esters by reacting at least stoichiometric quantities of an alcohol with a mixture of carbon monoxide and oxygen, which process is carried out at elevated temperatures and pressures in the presence of a catalyst which comprises a mixture of a metal salt compound, a catalytic amount of an amine base, a metal oxidant salt compound and an acid or an ammonium or substituted ammonium salt compound to provide a pronounced effect on oxalate ester selectivity, and high conversions to the oxalates over the carbonates and other side reaction products which may be present in only trace amounts. In addition, it has been found that alternatively catalytic amounts of various ligands, which will not work in themselves, may be used in conjunction with the metal salt compounds, the amines, the amine salts and the oxidant salts.

It is a primary object of this invention to provide a process for the preparation of oxalate esters in high yield and high conversion of reactants while avoiding operational problems associated with prior processes.

It is another object of this invention to provide a novel reaction system useful in the conversion of carbon monoxide, oxygen and alcohol to oxalate esters.

It is a further object of this invention to provide a specific catalytic mechanism for the employment of metal salt compounds, oxidant salts, amine salts and amines or ammonia as a catalytic mixture in an oxidative carbonylation process employing alcohol, carbon monoxide and oxygen as reactants.

These and other objects and advantages of this invention will become apparent from the description of the invention which follows and from the claims.

DESCRIPTION OF THE INVENTION

In accordance with the invention, an oxalate ester is produced by reacting, under liquid phase conditions, a mixture of carbon monoxide and oxygen with an alcohol, preferably an aliphatic alcohol, at elevated temperatures and pressures in the presence of a catalyst system comprising a mixture of (1) palladium, rhodium, platinum, copper, or cadmium metal or metal salt compound or mixture thereof, with or without a ligand or coordination complex compound such as lithium iodide, and (2) ammonia or a primary, secondary or tertiary amine, in addition to (3) catalytic amounts of a copper (I), copper (II), iron (II) or iron (III) metal oxidant salt and (4) an ammonium salt or amine salt or acid stronger than water which will not complex too strongly with the metal salt compound.

As indicated hereinabove, catalytic amounts of an amine or ammonia are added to the reaction mixture in addition to catalytic amounts of a metal oxidant salt, an amine salt, and a metal salt compound of palladium, rhodium, platinum, copper, or cadmium or mixtures thereof. The amine salt so added may also be formed in situ in the reaction mixture by the addition of an acid such as sulfuric acid in order to form the necessary quantity of amine salt. Thus, for example, triethylamine can be employed initially in sufficient amounts and sulfuric acid added to form triethylammonium sulfate in the desired catalytic quantities. The addition of the amine and the acid to form the amine salt must be closely controlled in order to establish a balance between the amine base and the amine salt compound.

The reaction between the alcohol, carbon monoxide, and oxygen may be carried out in an autoclave or any other high pressure reactor. Although the order of addition of reactants and the components forming the catalyst mixture may vary, a general procedure is to charge the alcohol, amine, amine salt (or the required amount of amine and acid), metal salt compound and the oxidant salt compound into the reaction vessel, and if desired a ligand or coordination complex, then introduce the proper amount of carbon monoxide and oxygen to the desired reaction pressure and then heat the mixture to the desired temperature for the appropriate period. The reaction can be carried out batchwise or as a continuous process and the order of addition of the reactants may also be varied to suit the particular apparatus employed. The addition of the oxygen or oxygen-containing gas, such as air, can be a pulsed or continuous addition to the reaction system. The reaction products are recovered and treated by any conventional method such as distillation and/or filtration, etc. to effect separation of the oxalate ester from unreacted materials, amine, oxidant salt, amine salt, metal salt compound, by products, etc.

The alcohols which may be employed in concentrations of from about 50 to 99.7 weight percent, preferably 77 to 94 weight percent and suitable for use in the process of the present invention can be monohydric saturated aliphatic, alicyclic or aralkyl alcohols and may contain other substituents such as amido, alkoxy, amino, carboxy, cyano, etc. radicals in addition to the hydroxyl group. The substituents, in general, do not interfere with the reaction of the invention.

The alcohols which are employed may be primary, secondary, or tertiary alcohols and conform to the general formula ROH, wherein R is an optionally substituted aliphatic, or alicyclic group containing from 1 to 20 carbon atoms and preferably unsubstituted aliphatic alcohols containing from 1 to 8 carbon atoms. R may also be an unsubstituted or substituted aralkyl group. Representative alcohols especially suitable for use in this invention are saturated monohydric alcohols such as methyl, ethyl, n-, iso-, sec-, and tert-butyl, amyl, hexyl, octyl, lauryl, n- and iso- propyl, cetyl, benzyl, chlorobenzyl and methoxy-benzyl alcohols as well as, for example, tolylcarbinol, cyclohexanol, heptanols, decanols, undecanols, 2-ethyl hexanol, nonanol, myristyl alcohol, stearyl alcohol, methyl cyclohexanol, pentadecanol, oleyl and eicosonyl alcohols, and the like. The preferred alcohols are the primary and secondary monohydric saturated aliphatic alcohols, such as methanol, ethanol, 1- and 2-propanol, n-butyl alcohol etc., up to 8 carbon atoms.

The amines employed in the catalyst component mixture in at least catalytic quantities in the process of the invention, in addition to ammonia, may be primary, secondary, or tertiary amines and include aliphatic, cycloaliphatic, aromatic and heterocyclic amines or mixtures thereof. The amines may be unsubstituted or contain other substituents such as halides, alkyl, aryl, hydroxy, amino, alkylamino, carboxy, etc. The amines may be employed as part of the catalyst system in the reaction in concentrations of from 0.1 to 10 weight percent and preferably at a concentration of from 0.3 to 4 weight percent as the free amine.

Representative amines as hereinabove described include for example, mono-, di- and tri-methyl, ethyl and propyl amines, iso- and diisopropylamines, allyl amines, mono-, di-, tri-, iso- and diisobutyl amines, 1-methylpropyl amine, 1,1-dimethylethyl amine, amyl amines, cyclohexyl amine, dicyclohexylamine, 1,3-dimethyl-butyl amine, 2-ethylhexylamine, 1-cyclopentyl-2-amino propane, 1,1,3-tetramethylbutylamine, aniline, ethylene diamine, methylene diamine, ethanolamine, octylamines, n-decyl amine, do-, tetra-, hexa-, oct-, dido-, ditetra-, diocta-, trido- and triocta-decylamines, chloroanilines, nitroanilines, toluidines, naphthylamine, N-methyl and N,N-ethyl, and N,N-dimethyl and N,N-diethyl aniline, di- and triphenylamines, N,N-diamylaniline, benzyl dimethyl amine, piperidine, pyrrolidine, etc. The preferred amines are the tertiary amines such as triethylamine and tributyl amine.

The metal salt compounds which may be employed in the process of this invention in the catalyst mixture are the palladium, platinum, rhodium, copper, and cadmium salts or mixtures thereof. Among the chemical forms of the metal salt compounds which can be used as such or as mixtures or formed in the reaction system from the metals per se are the palladium, platinum and rhodium, halides, sulfates, oxalates and acetates and the copper halides, preferably the palladium (II) sulfate and palladium (II) and copper (I) or (II) halides such as palladium (II) iodide, and copper (I) iodide. Representative catalytic metal salt compounds include, for example palladium (II) chloride, copper (II) chloride, rhodium (III) chloride, copper (I) iodide, palladium (II) sulfate, palladium (II) acetate, palladium (II) iodide, rhodium (III) bromide, platinum (II) chloride, platinum (II) sulfate, cadmium chloride, etc. As indicated above the metals as such may be added to the reaction as part of the catalyst mixture, the salt compound being formed in situ from at least a portion of the metal under reaction conditions.

The palladium, platinum, rhodium, copper, and cadmium compounds employed may be in a homogeneous state in the reaction mixture at reaction conditions. Thus, the compounds may be present in solution, or suspension and may also be on support materials such as alumina, silica gel, aluminosilicates, activated carbon or zeolites. The compounds may be partially or completely soluble under reaction conditions. The reaction is generally carried out in the presence of a catalytic proportion of the metal salt compound and will proceed with small amounts of the metal salt compounds hereinabove described. Generally the proportions of the metal salt compound used in the reaction will be equivalent to between about 0.001 to 5 weight percent of the alcohol employed and are preferably employed in amounts between about 0.01 to 2 percent by weight of the alcohol employed. Larger or smaller amounts may be employed at varied pressures and temperatures.

As mentioned hereinabove, alternatively, a ligand or coordination complex compound of the metal salt compound may be employed in the process of the invention in the catalytic mixture and thereby also achieve a pronounced increase in the selectivity for the oxalate ester. The ligands may be, for example, alkyl or aryl phosphines arsines, or stibines or halide salts, such as lithium iodide, ammonium chloride, and triethylammonium iodide, etc. The complexes of the metal salt compounds which are suitable for use in the process of the present invention include complex compounds of palladium, platinum, rhodium, cadmium, and copper. The complex compounds may contain one or more atoms of the said metals in the molecule and when more than one such atom is present, the metals may be the same or different. The mono- or polydentate ligands which are present in the molecule of the complex compounds and in which at least one of the electrondonating atoms is an atom of phosphorous, arsenic or antimony or a halide ion containing a lone pair of electrons may be, for example, organo-phosphines, -arsines and -stibines. Suitable mono-dentate ligands include alkyl phosphines such as trimethylphosphine and tributylphosphine, aryl-phosphines such as diethylphenylphosphine and radicals derived from such phosphines, for example the radical having the formula $—P(CH_3)_2$. Hydrocarbyloxy phosphines, i.e., phosphites, such as triphenyl phosphite may also be employed. Suitable polydentate ligands include tetramethyl diphosphinoethane and tetraphenyl diphosphinoethane. Exactly analogous derivatives of arsenic and antimony may be used; however, because of their greater ease of preparation and stability of the derived complexes, the hydrocarbyl derivatives of phosphorus are preferred. It is preferred to employ the alkali metal iodides, e.g. lithium iodide, or an ammonium or substituted ammonium iodides, e.g. triethyl ammonium iodide.

The complex compounds suitable for use in the process of the present invention may contain in the molecule, in addition to the ligands discussed above, one or more other atoms, groups or molecules, which are chemically bonded to the metal atom or atoms. Atoms which may be bonded to the metal include, for example, hydrogen, nitrogen and halogen atoms; groups which may be bonded to the metal include, for example hydrocarbyl, hydrocarbyloxy, carbonyl, nitrosyl, cyano and $SnCl_3—$ groups; molecules which may be bonded to the metal include, for example organic isocyanides and isothiocyanates. Examples of suitable complex compounds are those represented by the following formulae:

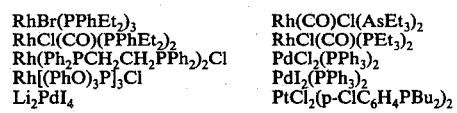

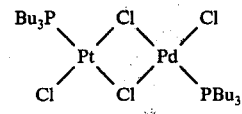

The complex compounds employed may be introduced into the reaction mixture as such, or they may be formed in situ from a suitable metal or metal compound noted above and the desired ligand.

The ligand or complex compounds may be used in catalytic amounts of from 0 to 3 percent preferably from 0.1 to 1 percent by weight of the alcohol to be reacted although larger or smaller amounts may be employed at varied pressures or reaction rates.

The oxidant salt compounds which may be employed in an anhydrous condition in the catalyst component mixture and in catalytic amounts of from 0.1 to 10 weight percent preferably 2 to 6 weight percent in the process of the invention include the iron (II), iron (III), copper (I) and copper (II) salts such as the halides, sulfates, trifluoroacetates, oxalates, naphthenates, or acetates preferably the copper (II) sulfate and trifluoroacetate, copper (I) iodide and iron (III) sulfate. Representative oxidant salts include, for example, copper (II) sulfate, copper (II) trifluoroacetate, copper (II) acetate, copper (II) oxalate, copper (II) triflate and copper (II) fluorosulfonate, copper (I) chloride, copper (I) sulfate, iron (III) sulfate, iron (II) iodide, iron (II) chloride, iron (III) acetate, iron (III) oxalate and iron (III) trifluoroacetate.

While halides may be employed in the process of this invention, excess halides in the form of oxidant salts, ligand or coordination complex compounds, and metal salt compounds may be detrimental to the reaction system of the present invention giving low yield of oxalates esters.

The ammonium or amine salts which are an important and required part of the catalytic component mixture are employed in an anhydrous condition and in a catalytic amount of from 0.1 to 40 weight percent preferably in a concentration of from 2 to 20 weight percent in the process of the invention include, for example, the ammonium and substituted ammonium sulfates, formates, trifluoroacetates, and acetates, preferably the tertiary amine sulfates such as triethylammonium hydrogen sulfate and triethylammonium sulfate. The salt may be present in the reaction system only in equilibrium amounts. Representative amine salts include, for example, diethylammonium sulfate, ethylammonium sulfate, butylammonium sulfate, ammonium sulfate, trimethylammonium sulfate, monomethylammonium sulfate, trimethylammonium hydrogen sulfate, ammonium acetate, triethylammonium formate, ammonium trifluoroacetate, methyl-, ethyl- and butyl- ammonium- trifluoroacetate, etc.

The ammonium or amine salts may be added as such or formed in situ in the required amounts upon the addition of an acid, such as sulfuric, benzene sulfonic, phosphoric, o-boric, p-toluene sulfonic, acetic or trifluoroacetic, to the reaction mixture while using greater than the required quantities of the amine base. The acids which may be used to form the salt include those which do not form a complex with the metal salt compound of the catalytic mixture or the metal oxidant salt compounds inactivating the catalyst and oxidant. As indicated hereinabove, the acids must be of sufficient strength, i.e., stronger than water, and such that the anion will not substantially complex with the metal salt or oxidant salt employed in the catalytic mixture. The salts which may be formed in situ may in themselves not necessarily be isolable and may exist in equilibrium in the reaction mixture under carbonylation reaction conditions. Thus, such salts could not be added per se but, as indicated above may be formed in situ upon the addition of a suitable acid to the reaction mixture containing an excess of an amine.

Although not required, solvents, if desired, which are chemically inert to the compounds of the reaction system may be employed. Suitable solvents include, for example, organic esters such as ethyl acetate, n-propyl formate, isopropyl acetate, sec- and iso-butyl acetate, amyl acetate, cyclohexyl acetate, n-propyl benzoate, lower alkyl phthalates, etc. and the alkyl sulfones and sulfoxides such as propyl ethyl sulfoxide, diisopropyl sulfone, diisooctyl sulfoxide, acetone, cyclohexanone, methyl formate, etc.

As indicated above the reaction can be suitably performed by introducing the oxygen and carbon monoxide at a desired pressure into contact with the alcohol/catalyst mixture comprising the metal salt compound, amine, an amine salt and oxidant salt and possibly a ligand or coordination complex and heating to the desired temperature. In general, a carbon monoxide pressure of about 500 psig to about 5000 psig partial pressure and preferably from 900 psig to about 2200 psig is employed. Stoichiometric quantities of carbon monoxide are generally employed. However, an excess of carbon monoxide may be employed, for example, in continuous processes where large excess of or high carbon monoxide requirements are generally utilized, a suitable recycle of the unreacted carbon monoxide may be employed. The reaction will proceed at temperatures of from about 40° C. to 150° C. It is generally preferred to operate the process at temperatures in the range of 60° C. to 100° C. to obtain a convenient rate of reaction. Heating and/or cooling means may be employed interior and/or exterior of the reaction to maintain the temperature within the desired range.

At least stoichiometric amounts of oxygen or an oxygen-containing gas such as air may be employed and at any oxygen partial pressure such that the explosive range is avoided. Thus, the concentrations of oxygen should be low enough so that the reaction mixture is not potentially explosive. The Handbook of Chemistry and Physics, 48th Edition, 1967 indicates that the explosive limits of pure oxygen in carbon monoxide is 6.1 to 84.5 volume percent and air in carbon monoxide to be 25.8 to 87.5 volume percent.

The reaction time is generally dependent upon the alcohol being reacted, temperature, pressure and on the amount and type of the catalyst mixture being charged as well as the type of equipment being employed. Reaction times will vary dependent on whether the process is continuous or batch.

The following examples are provided to illustrate the invention in accordance with the principles of this invention but are not to be construed as limiting the invention in any way except as indicated by the appended claims.

EXAMPLES 1 to 12

In Examples 1–12 which follow, a solution of the amine, the amine salt, and ligand in the alcohol was charged to a 300 ml. stainless steel stirred autoclave. The metal salt compound, and oxidant salt compound were charged to the autoclave as solids. Carbon monoxide was charged to 1800 psig and the autoclave heated to reaction temperature with stirring of 1000 rpm. Compressed air or oxygen was charged to the autoclave so that the gas mixture was not potentially explosive and an exotherm and pressure drop noted. When the reaction subsided, additional air or oxygen was charged to the autoclave. The air or oxygen charging was repeated until no further reaction was evident. Where oxygen was employed, CO was pulsed into the autoclave after the oxygen charge in order to replace the CO that was consumed after the previous oxygen charge.

Upon completion of the reaction, the reactor was cooled to ambient temperature and vented to ambient pressure and gas samples obtained. Precipitated solids were separated from the liquid by vacuum filtration. The liquid product was analyzed by gas-liquid chromatography (glc) and the gaseous product was analysed by mass spectral analysis (MS).

Alcohol conversions were calculated only on the basis of moles of carbonate ester and oxalate ester formed by the reaction. Side products such as formate ester, etc. were not considered as converted alcohol.

The catalyst mixture, reactants, and conditions employed for Examples 1–12 are shown in Table 1 and the results are summarized in Table 2. Examples 8, 10 and 11 are comparative Examples.

TABLE 1

| | Catalyst | | | | | Reactants and Conditions | | | | |
|---|---|---|---|---|---|---|---|---|---|---|
| 1 | 2 | 3 | 4 | 5 | 6 | 7 | 8 | 9 | 10 | 11 |
| 1 | PdI$_2$ .51g. (1.41 mmoles) | $\phi_3$P .74g. (2.82 mmoles) | TEA 9.4g. (92.5 mmoles) | TEAS 13.9g. (46.3 mmoles) | CuSO$_4$ 14.7g. (92.5 mmoles) | iPrOH 54.9g. (0.914 moles) | 65 | 1875–2230 | Air 965 | 214 |
| 2 | PdI$_2$ .25g. (0.70 mmoles) | $\phi_3$P .37g. (1.41 mmoles) | TEA 2.3g. (23 mmoles) | TEAS 3.6g. (12 mmoles) | CuSO$_4$ 3.7g. (23 mmoles) | iPrOH 54.9g. (0.914 moles) | 60 | 1910–2340 | Air 2185 | 601 |
| 3 | PdI$_2$ .26g. (0.71 mmoles) | $\phi_3$P .37g. (1.41 mmoles) | TEA 0.6g. (6.0 mmoles) | TEAS 0.9g. (3.0 mmoles) | CuSO$_4$ .96g. (6.0 mmoles) | iPrOH 54.9g. (0.914 moles) | 70 | 2335–2380 | Air 585 | 122 |
| 4 | PdI$_2$ .26g. (0.71 mmoles) | LiI .19g. (1.41 mmoles) | TEA 2.3g. (23 mmoles) | TEAS 3.5g. (11.6 mmoles) | CuSO$_4$ 3.7g. (23 mmoles) | MeOH 55.4g. (1.73 moles) | 60 | 2110–2380 | Air 1675 | 154 |
| 5 | PdI$_2$ .25g. (0.69 mmoles) | LiI .19g. (1.41 mmoles) | TEA 2.3g. (23 mmoles) | TEAS 6.9g. (23 mmoles) | CuSO$_4$ 3.7g. (23 mmoles) | MeOH 55.4g. (1.73 moles) | 60 | 2100–2410 | Air 1955 | 208 |
| 6 | PdI$_2$ .25g. (0.70 mmoles) | LiI .19g. (1.41 mmoles) | TEA 2.3g. (23 mmoles) | TEAS 3.5g. (11.6 mmoles) | CuSO$_4$ 3.7g. (23 mmoles) | EtOH 55.2g. (1.20 moles) | 60 | 2045–2420 | Air 1980 | 339 |
| 7 | PdI$_2$ .25g. (0.70 mmoles) | $\phi_3$P .74g. (2.82 mmoles) | TEA 2.5g. (25 mmoles) | N. Acids (7.0g.) | Cu Nap. (5.0g.) | nC$_8$H$_{17}$OH 57.3g. (0.44 moles) | 60 | 2305–2430 | Air 2195 | 267 |
| *8 | PdI$_2$ .25g. (0.69 mmoles) | — | TEA 2.3g. (23 mmoles) | TEAS 4.5g. (15 mmoles) | Chloranil 5.6g. (23 mmoles) | MeOH 55.4g. (1.73 moles) | 60 | 2380 | Air 650 | 73 |
| 9 | PdI$_2$ .25g. (0.69 mmoles) | LiI .19g. (1.41 mmoles) | TEA 2.3g. (23 mmoles) | TEAS 6.9g. (23 mmoles) | CuSO$_4$ 3.7g. (23 mmoles) | MeOH 55.4g. (1.73 moles) | 60 | 1650–1975 | O$_2$ 200 | 155 |
| *10 | PdI$_2$ .25g. (0.69 mmoles) | LiI .19g. (1.41 mmoles) | TEA 2.3g. (23 mmoles) | TEAS 6.9g. (23 mmoles) | CuSO$_4$ 3.7g. (23 mmoles) | H$_2$O 70.2g. (3.9 moles) | 60 | 1500–2000 | O$_2$ 100 | 27 |
| *11 | PdI$_2$ .25g. (0.69 mmoles) | LiI .19g. (1.41 mmoles) | TEA 2.3g. (23 mmoles) | Pyridine 11g. (138 mmoles) | CuSO$_4$ 3.7g. (23 mmoles) | MeOH 55.4g. (1.73 moles) | 125 | 1690–2170 | O$_2$ 100 | 109 |
| 12 | CuI .27g.$^{(1)}$ (1.41 mmoles) | LiI .38g. (2.82 mmoles) | TEA 2.3g. (23 mmoles) | TEAS 6.9g. (23 mmoles) | CuSO$_4$ 3.7g. (23 mmoles) | MeOH 55.4g. (1.73 moles) | 100 | 2445–2650 | Air 695 | 91 |

The following abbreviations were used in this Table: TEA — triethylamine; TEAS — triethylammonium sulfate; Cu Nap. — copper (II) naphthenates; N. Acids — naphthenic acids; iPrOH — 2-propanol; MeOH — methanol; EtOH — ethanol; $\phi_3$P — triphenylphosphine
*Comparative Examples
$^{(1)}$Mixture of .01 grams (.092 mmoles) palladium with the CuI.

COLUMN HEADINGS FOR TABLE 1

1. Example No.
2. Metal Salt Compound
3. Ligand or Coordination Complex
4. Amine
5. Amine Salt Compound
6. Oxidant Salt Compound
   Reactants and Conditions
7. Alcohol (moles)
8. Temperature ° C.
9. Total Pressure (psig)
10. Total Air/O$_2$ Charged (psig)
11. Reaction Time (minutes)

TABLE 2

| Example No. | Conversion of Alcohol (mole %) | Yield (moles) | | |
|---|---|---|---|---|
| | | CO$_2$ | Carbonate Ester | Oxalate Ester |
| 1 | 15.3 | 0.056 | 0.0 | 0.070 |
| 2 | 18.4 | 0.181 | 0.0 | 0.084 |
| 3 | 3.1 | 0.0 | 0.0 | 0.014 |
| 4 | 14.7 | 0.05 | trace | 0.127 |
| 5 | 15.7 | 0.085 | trace | 0.136 |
| 6 | 15.2 | 0.15 | 0.001 | 0.090 |
| 7 | — | — | — | (1) |
| *8 | 0.0 | 0.0 | 0.0 | trace |
| 9 | 11.3 | 0.049 | 0.0 | 0.098 |
| *10 | 0.0 | — | 0.0 | 0.0 |
| *11 | 2.0 | 0.032 | 0.017 | 0.0 |
| 12 | 8.1 | 0.028 | 0.01 | 0.06 |

$^{(1)}$Reaction product showed the presence of a carbonyl band in the ir spectrum. A solid containing copper oxalate (CuC$_2$O$_4$ . $\frac{1}{2}$H$_2$O) was filtered from the reaction product.
*Comparative Examples

EXAMPLES 13 to 24

In Examples 13 to 24 which follow, a solution of the amine, sulfuric acid, and the alcohol was charged to a 500 ml. stainless steel stirred autoclave equipped with a condenser ($\sim -20°$ C.) and a liquid separator on the downstream side. The metal salt compound, ligand, and oxidant salt compound were charged to the autoclave as solids. Carbon monoxide was charged to the autoclave to 1800 psig and the autoclave heated to temperature with stirring at a rate of 1500 rpm. The carbon monoxide flow rate was established to maintain the pressure at 1800 psig and an air flow started. An immediate exotherm was noted in most cases. A constant temperature was maintained with tap water ($\pm 1°$ C.). Gas samples of the effluent gases were collected periodically throughout the run and analyzed for CO$_2$ by mass spectral analysis.

The reaction was discontinued by cooling to ambient temperature with tap water. The gas flows were stopped and the reactor vented. During venting, gas samples were collected and analyzed for carbon dioxide.

The liquid product was analyzed by gas-liquid chromatrography after vacuum filtration to separate the precipitated solids from the liquid product.

Alcohol conversions were calculated on the basis of the alcohol required to form the yield amounts of oxalate esters carbonate esters and any formate esters produced. Selectivities were calculated on the basis of the amount of CO consumed to produce CO$_2$, oxalate, carbonate, and formate, and are the only detectible compounds which result from CO consumption in the reaction.

The catalyst mixture, reactants, and conditions employed (Examples 13 to 24) are shown in Table 3 and the results are summarized in Table 4.

n-butyl alcohol (2.19 moles) was charged to a 500 ml stainless steel stirred autoclave. Palladium (II) iodide (2.0 mmoles), copper (I) iodide (4.0 mmoles), and lith-

TABLE 3

| | Catalyst | | | | | Reactants and Conditions | | | | |
|---|---|---|---|---|---|---|---|---|---|---|
| 1 | 2 | 3 | 4 | 5 | 6 — $H_2SO_4$ | 7 | 8 | 9 | 10 | 11 |
| 13 | $PdI_2$ .36g. (1.0 mmoles) | LiI .27g. (2.0 mmoles) | $CuSO_4$ 5.2g. (32.4 mmoles) | TEA 10g. (100 mmoles) | 3.42g. (33.7 mmoles) | MeOH 158.2g. (4.94 moles) | 100 | 4.35 | 1.38 | 15 |
| 14 | $PdI_2$ .36g. (1.0 mmoles) | LiI .27g. (2.0 mmoles) | $CuSO_4$ 5.2g. (32.4 mmoles) | TEA 10g. (100 mmoles) | 3.42g. (33.7 mmoles) | MeOH 158.2g. (4.94 moles) | 70 | 4.35 | 1.38 | 110 |
| 15 | $PdI_2$ .36g. (1.0 mmoles) | LiI .27g. (2.0 mmoles) | $CuSO_4$ 5.2g. (32.4 mmoles) | TEA 10g. (100 mmoles) | 3.42g. (33.7 mmoles) | MeOH 158.2g. (4.94 moles) | 70 | 4.35 | 1.38 | 90 |
| 16 | $PdI_2$ .36g. (1.0 mmoles) | LiI .27g. (2.0 mmoles) | $CuSO_4$ 5.2g. (32.4 mmoles) | TEA 10g. (100 mmoles) | 3.42g. (33.7 mmoles) | MeOH 158.2g. (4.94 moles) | 60 | 3.22 | 1.38 | 117 |
| 17 | $PdSO_4$ .24g. (1.0 mmoles) | — | $CuSO_4$ 5.2g. (32.4 mmoles) | TEA 10g. (100 mmoles) | 3.42g. (33.7 mmoles) | MeOH 158.2g. (4.94 moles) | 70 | 4.35 | 1.38 | 180 |
| 18 | $PdI_2$ .72g. (2.0 mmoles) | LiI .53g. (4.0 mmoles) | $CuSO_4$ 10.3g. (64.8 mmoles) | TEA 20g. (200 mmoles) | 6.85g. (67.4 mmoles) | MeOH 158.2g. (4.94 moles) | 70 | 4.35 | 1.38 | 120 |
| 19 | $PdI_2$ .36g. (1.0 mmoles) | LiI .28g. (2.0 mmoles) | $CuSO_4$ 5.2g. (32.4 mmoles) | TEA 5g. (50 mmoles) | 1.72g. (16.9 mmoles) | MeOH 158.2g. (4.94 moles) | 70 | 4.35 | 1.38 | 120 |
| 20 | $PdI_2$ .36g. (1.0 mmoles) | LiI .28g. (2.0 mmoles) | $CuSO_4$ 5.2g. (32.4 mmoles) | TEA 4.2g. (42.1 mmoles) | 1.72g. (16.9 mmoles) | MeOH 158.2g. (4.94 moles) | 70 | 4.35 | 1.38 | 120 |
| 21 | $PdI_2$ .36g. (1.0 mmoles) | LiI .28g. (2.0 mmoles) | $CuSO_4$ 5.2g. (32.4 mmoles) | TEA 4.2g. (42.1 mmoles) | 1.72g. (16.9 mmoles) | MeOH 158.2g. (4.94 moles) | 60 | 4.35 | 1.38 | 120 |
| 22 | CuI .38g. (2.0 mmoles) | LiI .53g. (4.0 mmoles) | $CuSO_4$ 5.2g. (32.4 mmoles) | TEA 5g. (50 mmoles) | 1.72g. (16.9 mmoles) | MeOH 158.2g. (4.94 moles) | 100 | 4.35 | 1.38 | 150 |
| 23 | $PdI_2$ .36g. (1.0 mmoles) | LiI .27g. (2.0 mmoles) | $CuSO_4$ 5.2g. (32.4 mmoles) | TEA 5g. (50 mmoles) | 1.72g. (16.9 mmoles) | EtOH 227.5g. (4.94 moles) | 70 | 4.35 | 1.38 | 150 |
| 24 | $PdI_2$ .36g. (1.0 mmoles) | LiI .27g. (2.0 mmoles) | $CuSO_4$ .63g. (4.0 mmoles) | TEA 2.5g. (25 mmoles) | .86g. (8.45 mmoles) | MeOH 158.2g. (4.94 moles) | 70 | 4.35 | 1.38 | 120 |

The following abbreviations were used in this Table: TEA — triethylamine; MeOH — methanol; EtOH — ethanol

COLUMN HEADINGS FOR TABLE 3

1. Example No.
   Catalyst (mmoles)
2. Metal Salt Compound
3. Ligand or Coordination Complex
4. Oxidant Salt Compound
5. Amine.
6. Acid (Sulfuric Acid)
   Reactants and Conditions
7. Alcohol (moles)
8. Temperature ° C.
9. CO Flow (l/min.)
10. Air Flow (l/min.)
11. Reaction Time (minutes)

ium sulfate monohydrate (8.0 mmoles) were charged to the autoclave as solids. Carbon monoxide was charged to the autoclave to 1070 psig, and the autoclave was heated to 70° C. with sitrring at a rate of 1500 rpm. Stirring was discontinued while air was charged to give a total pressure of 1800 psig. A carbon monoxide flow rate of 4.0 l/min. and an air flow rate of 2.7 l/min. were established at 1800 psig. Stirring was started. The contents were allowed to react for 45 minutes, during which time gas samples of the effluent gases were collected periodically throughout the run and were analyzed for carbon dioxide.

The autoclave was cooled to ambient temperature with tap water. The gas flows were stopped, and the reactor was vented. The vent gases were collected and

TABLE 4

| | Yield | | | | Conversion | Selectivities (mole %) | | | |
|---|---|---|---|---|---|---|---|---|---|
| Example No. | Formate Ester | Carbonate Ester | Oxalate Ester | $CO_2$ | % Alcohol (mole%) | Formate Ester | Carbonate Ester | Oxalate Ester | $CO_2$ |
| 13 | — | ≦0.01 | 0.055 | 0.008 | 2.7 | 0.0 | ≦9.2 | 84.6 | 6.2 |
| 14 | 0.025 | 0.008 | 0.304 | 0.11 | 13.1 | 3.3 | 1.1 | 81.0 | 14.6 |
| 15 | 0.025 | <0.005 | 0.334 | 0.09 | 14.2 | 3.2 | <0.6 | 84.8 | 11.4 |
| 16 | 0.006 | 0.006 | 0.35 | 0.09 | 14.5 | 0.7 | 0.7 | 87.3 | 11.2 |
| 17 | 0.030 | 0.009 | 0.324 | 0.14 | 14.1 | 3.6 | 1.1 | 78.4 | 16.9 |
| 18 | 0.052 | 0.008 | 0.422 | — | 18.5 | — | — | — | — |
| 19 | 0.044 | trace | 0.415 | 0.27 | 17.7 | 3.8 | 0.0 | 72.6 | 23.6 |
| 20 | 0.032 | 0.000 | 0.356 | 0.26 | 15.1 | 3.2 | 0.0 | 70.9 | 25.9 |
| 21 | 0.024 | 0.000 | 0.266 | 0.17 | 11.3 | 3.3 | 0.0 | 73.3 | 23.4 |
| 22 | <0.003 | <0.004 | 0.130 | 0.13 | 5.3 | 0.0 | 0.0 | 66.7 | 33.3 |
| 23 | <0.001 | 0.009 | 0.398 | 0.26 | 16.5 | 0.0 | 0.8 | 74.7 | 24.4 |
| 24 | 0.00 | 0.00 | 0.056 | — | 2.3 | 0.0 | 0.0 | — | — |

EXAMPLE 25

A solution of triethylamine (197.6 mmoles), concentrated (96.4 percent) sulfuric acid (68.0 mmoles), and analyzed for carbon dioxide. The liquid product was anaylzed by gas-liquid chromatography after vacuum filtration to separate the precipitated solids from the liquid product. Analysis showed 0.023 mole dibutyl carbonate, and 0.267 mole dibutyl oxalate. The gases contained 0.165 mole carbon dioxide. Other oxalate-containing salts (0.040 mole) were detected in the liquid product.

EXAMPLE 26

A solution of 84.2 mmoles of triethylamine, 33.8 mmoles of 96.4 percent sulfuric acid, 1.0 mmole lithium iodide and 1.71 moles of ethyl alcohol was charged to a 300 ml. stainless steel stirring autoclave together with 1.0 mmole copper (I) iodide and 23.0 mmoles copper (II) sulfate charged as solids. Carbon monoxide was charged to the autoclave to a pressure of 1000 psig and the autoclave heated to 100° C. with stirring. Pressure was then adjusted to 1500 psig with carbon monoxide. 100 psig oxygen was charged to the autoclave followed by an additional 200 psig CO. An additional 100 psig $O_2$ and 200 psig CO was charged. Total reaction pressures were between 1800–2100 psig. The reaction was maintained at 100° C. for 90 minutes after which the reactor was cooled to ambient temperature and vented to ambient pressure. A gas sample was obtained at 1000 psig. The solids were separated from the liquid by vacuum filtration. The liquid product was analyzed by gas-liquid chromatography, and the gaseous product was analyzed by mass spectral analysis and showed 0.010 mole diethyl carbonate, 0.004 mole diethyl oxalate, and 0.015 mole of carbon dioxide produced. Alcohol conversion was 1.6 mole percent. Selectivities, in mole percent, calculated on the basis of carbon monoxide consumed showed 30.3 percent diethyl carbonate, 24.2 percent diethyl oxalate, and 45.5 percent $CO_2$.

EXAMPLE 27

The procedure of Example 26 was repeated with the exception that 1.0 mmoles of cadmium iodide was used in place of the copper (I) iodide in the catalyst system. Analysis of the liquid and gaseous products showed 0.010 mole diethyl carbonate, 0.005 mole diethyl oxalate, and 0.014 mole carbon dioxide. Alcohol conversion was 1.8 mole percent. Selectivities, in mole percent, were 29.4 diethyl carbonate, 29.4 diethyl oxalate, and 41.2 carbon dioxide.

EXAMPLE 28

A solution of 100 mmoles triethylamine, 68 mmoles triethylammonium bisulfate, and 2.19 moles of n-butyl alcohol was charged to a 500 ml stainless steel stirred autoclave equipped with a condenser and a liquid separator on the downstream side. 16.2 mmoles copper (II) sulfate and 0.30 mmoles of palladium metal on activated carbon were charged to the autoclave as solids. Carbon monoxide was charged to the autoclave to 1000 psig and the autoclave heated to 70° C. with stirring at a rate of 1500 rpm. A carbon monoxide flow rate of 4.35 l/min. was established to maintain the pressure at 1000 psig and a 1.60 l/min. air flow started. A reaction exotherm was noted. The reaction temperature of 70° C. was maintained with tap water (±1° C.). Gas samples of the effluent gases were collected periodically throughout the run and analyzed for carbon dioxide by mass spectral analysis.

The reaction was discontinued after 120 minutes by cooling to ambient temperature with tap water. The gas flows were stopped and the reactor vented. During venting, gas samples were collected and analyzed for carbon dioxide. The liquid product was analyzed by gas-liquid chromatography after vacuum filtration to separate the precipitated solids from the liquid product. Analysis showed 0.023 mole dibutyl carbonate, 0.171 mole dibutyl oxalate, and 0.14 mole carbon dioxide was produced. Alcohol conversion was calculated to be 17.7 mole percent. Selectivities, in mole percent, calculated on the basis of carbon monoxide consumed showed 4.6 percent dibutyl carbonate, 67.7 percent dibutyl oxalate and 27.7 percent carbon dioxide.

EXAMPLE 29

The procedure of Example 28 was repeated using a reaction mixture of 168.4 mmoles triethylamine, 68.0 mmoles of 96.4 percent sulfuric acid, 2.19 moles n-butyl alcohol, 0.30 mmole palladium bromide, and 16.2 mmoles copper (II) sulfate. The reaction was carried out at 500 psig at a temperature of 70° C. for 180 minutes with a carbon monoxide flow rate of 4.35 l/min. and an air flow rate of 1.60 l/min. Analysis of the reaction products showed 0.051 mole dibutyl carbonate, 0.154 mole dibutyl oxalate and 0.11 mole carbon dioxide. Alcohol conversion was calculated to be 18.7 mole percent. Selectivities were calculated to be 10.9 mole percent dibutyl carbonate, 65.7 mole percent dibutyl oxalate, and 23.5 mole percent carbon dioxide.

EXAMPLE 30 (Comparative)

The procedure as carried out in Examples 13 to 24 was repeated using a reaction mixture of 71 mmoles triethylamine, 2.19 moles n-butyl alcohol, 1.0 mmole palladium iodide, 2.0 mmoles lithium iodide, and 32.4 mmoles copper (II) sulfate. A constant reaction temperature of 70° C. was maintained for 120 minutes with a carbon monoxide flow rate of 3.22 l/min. and an air flow rate of 1.38 l/min. Analysis of the reaction products showed 0.001 mole dibutyl carbonate and 0.018 mole dibutyl oxalate. No carbon dioxide was detected. The alcohol conversion was calculated to be 1.7 mole percent. Selectivites were calculated to be 2.7 mole percent dibutyl carbonate, 97.3 mole percent dibutyl oxalate and 0.0 mole percent carbon dioxide.

EXAMPLES 31 to 43

In Examples 31 to 43 which follow in table form, the procedure and general operating conditions as employed in Examples 13 to 24 was repeated using a catalytic mixture of a metal salt compound, an oxidant salt compound, an amine, and an amine salt compound or an acid, with or without a ligand or coordination complex compound along with an appropriate alcohol reactant. Gaseous and liquid products were analyzed by mass spectral analysis and gas-liquid chromatography respectively. Alcohol conversions and selectivities were calculated as in Examples 13 to 24.

The catalyst mixtures, reactants and operating conditions employed (Examples 31 to 43) are set forth in Table 5 and the results are summarized in Table 6. Column headings are indicated.

TABLE 5

| | Catalyst (mmoles) | | | | | Reactants and Conditions | | | |
|---|---|---|---|---|---|---|---|---|---|
| 1 | 2 | 3 | 4 | 5 | 6 | 7 (moles) | 8 | 9 | 10 | 11 |
| 31 | $PtBr_2$ | — | $CuSO_4$ | | $Bu_3N$ | $H_2SO_4$ | nBuOH | 70 | 3.22 | 1.38 | 150 |

TABLE 5-continued

| 1 | 2 | 3 | 4 | 5 | 6 | 7 (moles) | 8 | 9 | 10 | 11 |
|---|---|---|---|---|---|---|---|---|---|---|
|   | 1.0 |   | 32.4 | 207 | 68.0 | 2.19 |   |   |   |   |
| 32 | RhCl$_3$ | — | CuSO$_4$ | Et$_2$NH | H$_2$SO$_4$ | NBuOH | 80 | 3.22 | 1.38 | 180 |
|   | 1.0 |   | 32.4 | 168.4 | 68.0 | 2.19 |   |   |   |   |
| 33 | CuI/CdI$_2$ | LiI | CuSO$_4$ | Et$_3$N | H$_2$SO$_4$ | EtOH | 120 | 3.22 | 1.05 | 180 |
|   | 1.0/1.0 | 1.0 | 32.4 | 50 | 16.9 | 3.43 |   |   |   |   |
| 34 | PdI$_2$ | LiI | CuC$_2$O$_4$·½H$_2$O | Et$_3$N | H$_2$SO$_4$ | EtOH | 70 | 3.22 | 1.38 | 60 |
|   | 1.0 | 1.0 | 32.4 | 50 | 16.9 | 4.94 |   |   |   |   |
| 35 | PdI$_2$ | LiI | CuSO$_4$ | Et$_3$N | H$_2$SO$_4$ | IBuOH | 70 | 3.22 | 1.38 | 120 |
|   | 1.0 | 2.0 | 32.4 | 50 | 16.9 | 2.19 |   |   |   |   |
| 36 | PdI$_2$ | LiI | CuSO$_4$ | Et$_3$N | H$_2$SO$_4$ | secBuOH | 70 | 3.22 | 1.38 | 120 |
|   | 2.8 | 14.9 | 32.4 | 50 | 16.9 | 2.18 |   |   |   |   |
| 37 | PdI$_2$ | LiI | CuSO$_4$ | Et$_3$N | H$_2$SO$_4$ | nBuOH | 70 | 3.22 | 1.38 | 120 |
|   | 1.0 | 2.0 | 32.4 | 207 | 68.0 | 2.19 |   |   |   |   |
| 38 | PdI$_2$ | LiI | CuSO$_4$ | NH$_3$ | (NH$_4$)$_2$SO$_4$ | EtOH | 70 | 3.22 | 1.38 | 120 |
|   | 1.0 | 2.0 | 32.4 | 17.0 | 16.9 | 4.94 |   |   |   |   |
| 39 | PdI$_2$ | LiI | CuO | Et$_3$N | H$_2$SO$_4$ | EtOH | 70 | 3.22 | 1.38 | 120 |
|   | 1.0 | 2.0 | 32.4 | 50 | 49.4 | 4.94 |   |   |   |   |
| 40 | PdCl$_2$ | — | Cu(OAc)$_2$ | Piperidine | CH$_3$COOH | MeOH | 60 | 3.22 | 1.38 | 150 |
|   | 1.0 |   | 32.4 | 50 | 25 | 4.94 |   |   |   |   |
| 41 | PdSO$_4$ | — | FeSO$_4$ | DMA | H$_2$SO$_4$ | n-octanol | 90 | 3.22 | 1.38 | 120 |
|   | 1.0 |   | 30.0 | 68.0 | 16.9 | 1.27 |   |   |   |   |
| 42 | PdC$_2$O$_4$ | $\phi_3$P | Cu(OOCH)$_2$ | Cyclohexyl-amine 50 | HCOOH | iPrOH | 50 | 3.22 | 1.00 | 1.20 |
|   | 1.0 | 4.0 | 32.4 |   | 25 | 2.61 |   |   |   |   |
| 43 | PtCl$_2$ | — | Cu(OOCCF$_3$)$_2$ | Et$_3$N | HOOCCF$_3$ | EtOH | 75 | 3.22 | 1.38 | 120 |
|   | 1.0 |   | 32.4 | 50 | 16.9 | 3.43 |   |   |   |   |

The folowing abbreviations were used in this Table:
$\phi_3$P — triphenylphosphine;
DMA — N,N-dimethylaniline

COLUMN HEADINGS FOR TABLE 5

1. Example No.
  Catalyst (mmoles)
2. Catalyst
3. Ligand
4. Oxidant Salt
5. Amine
6. Amine Salt or Acid
  Reactants and Conditions
7. Alcohol (moles)
8. Temperature ° C.
9. CO Flow (l/min.)
10. Air Flow (l/min.)
11. Reaction Time (minutes)

TABLE 6

| Example No. | Products (mmoles) | | | | Conversion of alcohol (mole %) | Selectivities (mole %) | | | |
|---|---|---|---|---|---|---|---|---|---|
| | Formate Ester | Carbonate Ester | Oxalate Ester | CO$_2$ | | Formate Ester | Carbonate Ester | Oxalate Ester | CO$_2$ |
| 31 | — | 0.021 | 0.181 | 0.07 | 18.4 | — | 4.6 | 79.9 | 15.5 |
| 32 | — | 0.023 | 0.172 | 0.10 | 17.8 | — | 4.9 | 73.7 | 21.4 |
| 33 | — | 0.120 | 0.075 | 0.05 | 11.4 | — | 37.5 | 46.9 | 15.6 |
| 34 | — | 0.000 | 0.043 | 0.003 | 1.7 | — | 0.0 | 96.6 | 3.4 |
| 35 | — | 0.006 | 0.152 | 0.065 | 14.8 | — | 1.6 | 80.2 | 17.2 |
| 36 | — | 0.000 | 0.165 | 0.34 | 15.2 | — | 0.0 | 49.4 | 50.6 |
| 37 | — | 0.016 | 0.200 | 0.07 | 19.7 | — | 3.3 | 82.3 | 14.4 |
| 38 | — | 0.000 | 0.133 | 0.09 | 7.4 | — | 0.0 | 74.7 | 25.3 |
| 39 | — | <0.004 | 0.206 | 0.51 | 13.0 | — | <0.4 | 44.5 | 55.1 |
| 40 | 0.026 | 0.008 | 0.431 | 0.08 | 18.3 | 2.7 | 0.8 | 88.3 | 8.2 |
| 41 | — | 0.001 | 0.074 | 0.32 | 11.8 | — | 0.2 | 31.6 | 68.2 |
| 42 | — | 0.016 | 0.156 | 0.020 | 13.2 | — | 10.8 | 75.7 | 13.5 |
| 43 | — | 0.043 | 0.163 | 0.17 | 12.0 | — | 8.0 | 60.5 | 31.5 |

EXAMPLE 44

The procedure, charge and conditions of Example 25 was repeated except that iron (II) iodide (4.0 mmoles) was charged to the atuoclave in place of copper (I) iodide, and the reaction time was carried out for 60 minutes.

Analysis of liquid and gaseous products showed 0.007 mole dibutyl carbonate, 0.082 mole dibutyl oxalate, 0.038 mole carbon dioxide, and 0.033 mole of other oxalate-containing salts.

EXAMPLES 45 to 49

Examples 45 to 49 which follow clearly show the advantage of employing an amine salt in the catalytic mixture of the invention. Example 45 is comparative in that no amine salt or acid to form same is employed. Examples 46 to 49 employ an amine salt (triethylammonium sulfate) in a range of weight percent concentrations.

In Examples 45 to 49 the procedure of Example 25 was repeated employing the same conditions with the exception that the reaction was carried out for 60 minutes. In each of the Examples a total of 62 mmoles of triethylamine was present in the catalyst mixture as free amine.

The amount of catalyst charged in millimoles, weight percent amine salt in solution, reactants and yield of dibutyl carbonate, dibutyl oxalate and carbon dioxide (CO$_2$) are summarized in Table 7.

TABLE 7

| Ex. No. | Catalyst charged (mmoles) | | | | | Wt. % (Et₃NH)₂SO₄⁽⁶⁾ in Charge solution | n-BuOH⁽³⁾ (moles) | Products (moles) | | |
|---|---|---|---|---|---|---|---|---|---|---|
| | PdI₂ | CuI | Et₃N⁽¹⁾ | H₂SO₄ | TEAHS⁽²⁾ | | | DBC⁽⁴⁾ | DBO⁽⁵⁾ | CO₂ |
| 45 | 2.0 | 4.0 | 61.6 | — | — | 0.00 | 2.19 | 0.009 | 0.098 | 0.105 |
| 46 | 2.0 | 4.0 | 63.6 | 1.0 | — | 0.17 | 2.19 | 0.013 | 0.136 | 0.116 |
| 47 | 2.0 | 4.0 | 73.4 | 11.8 | — | 2.1 | 2.19 | 0.015 | 0.165 | 0.121 |
| 48 | 2.0 | 4.0 | 652 | 295 | — | 34.2 | 2.19 | 0.019 | 0.228 | 0.136 |
| 49 | 2.0 | 4.0 | 212 | — | 150 | 21.0 | 2.19 | 0.041 | 0.291 | 0.197 |

⁽¹⁾Et₃N — triethylamine
⁽²⁾TEAHS — triethylammonium hydrogen sulfate
⁽³⁾n-BuOH — n-butyl alcohol
⁽⁴⁾DBC — dibutyl carbonate
⁽⁵⁾DBO — dibutyl oxalate
⁽⁶⁾(Et₃NH)₂SO₄ — triethylammonium sulfate

I claim:

1. A process for the preparation of oxalate esters of an alcohol which comprises reacting a monohydric saturated aliphatic, alicyclic or aralkyl alcohol containing from 1 to 20 carbon atoms and which may contain other substituents which do not interfere with the reaction, with a mixture of carbon monoxide and oxygen at a pressure of between about 500 psig to 5000 psig and at a temperature in the range of about 40° C. to 150° C. in the presence of an effective amount of a catalytic mixture of
 (a) a palladium, rhodium, platinum, copper or cadmium metal salt compound or mixtures thereof,
 (b) an aliphatic, cycloaliphatic aromatic or heterocyclic amine or ammonia,
 (c) a copper (I), copper (II), iron (II) or iron (III) oxidant salt compound and
 (d) from about 0.1 to 40 weight percent of an ammonium or substituted ammonium salt compound with a counterion other than a halide, and recovering the desired oxalate ester.

2. A process according to claim 1 wherein the alcohol is a monohydric saturated aliphatic alcohol containing from 1 to 8 carbon atoms.

3. A process according to claim 2 wherein the alcohol is selected from the group consisting of methanol, ethanol, propanol, a butanol and octanol.

4. A process according to claim 3 wherein the alcohol is methanol.

5. A process according to claim 3 wherein the alcohol is ethanol.

6. A process according to claim 3 wherein the alcohol is 2-propanol.

7. A process according to claim 3 wherein the alcohol is normal butyl, iso-butyl or sec-butyl alcohol.

8. A process according to claim 1 wherein the metal salt compound is selected from the group consisting of palladium, rhodium, platinum and cadmium, halides, oxalates, sulfates and acetates and copper halides or mixtures thereof.

9. A process according to claim 8 wherein the metal salt compound is selected from palladium iodide, palladium sulfate, palladium chloride, palladium bromide, platinum acetate, platinum chloride, platinum bromide, copper iodide, cadmium chloride, cadmium iodide, and rhodium chloride.

10. A process according to claim 9 wherein the metal salt compound is palladium iodide.

11. A process according to claim 9 wherein the metal salt compound is palladium sulfate.

12. A process according to claim 9 wherein the metal salt compound is copper iodide.

13. A process according to claim 1 wherein the amine is a primary, secondary or tertiary amine employed in concentrations of from 0.1 to 10 weight percent.

14. A process according to claim 13 wherein the amine is employed in concentrations of from 0.3 to 4 weight percent.

15. A process according to claim 13 wherein the amine is triethylamine.

16. A process according to claim 1 wherein the oxidant salt compound is a copper (I), copper (II), iron (II), or iron (III) halide, oxalate, sulfate, acetate, naphthenate or trifluoroacetate.

17. A process according to claim 16 wherein the oxidant salt is copper (I) iodide.

18. A process according to claim 16 wherein the oxidant salt is copper (II) sulfate.

19. A process according to claim 16 wherein the oxidant salt is copper oxalate.

20. A process according to claim 1 wherein the ammonium salt compound is selected from the group consisting of ammonium and substituted ammonium sulfates, trifluoroacetates and acetates.

21. A process according to claim 20 wherein the ammonium salt compound is triethylammonium sulfate.

22. A process according to claim 19 wherein the ammonium salt compound is triethylammonium hydrogen sulfate.

23. A process according to claim 1 wherein the ammonium salt compound is employed in concentrations of from 2 to 20 weight percent.

24. A process according to claim 1 wherein the ammonium or substituted ammonium salt compound is formed in situ upon the addition of an acid to the reaction mixture containing an excess of amine over the required quantities of said amine base in the catalytic mixture, said acid being of a strength stronger than water and such that the anion will not substantially complex with the metal salt or oxidant salt compound in said catalytic mixture.

25. A process according to claim 24 wherein said acid is sulfuric acid.

26. A process according to claim 1 wherein the reaction is carried out in the presence of a catalytic amount of an organic mono- or poly-dentate ligand or coordination complex selected from the group consisting of alkyl, aryl and halogen substituted phosphines, arsines, stibines and halide salts.

27. A process according to claim 26 wherein the ligand or coordination complex is triphenylphosphine.

28. A process according to claim 26 wherein the ligand or coordination complex is lithium iodide.

29. A process according to claim 1 wherein the pressure is between about 900 psig and 2200 psig and the temperature is in the range of 60° C. to 100° C.

30. A process according to claim 1 wherein the alcohol is selected from the group consisting of methanol, ethanol, 2-propanol and butanol, the metal salt compound is palladium iodide, the amine is triethylamine, the oxidant salt is copper (II) sulfate, and the ammonium salt compound is triethylammonium sulfate.

31. A process according to claim 30 wherein a catalytic amount of lithium iodide is added to the reaction mixture.

32. A process according to claim 1 wherein air is employed as a source of oxygen for the reaction.

33. A process according to claim 1 wherein the metal salt compound is supported.

34. A process according to claim 1 wherein the alcohol is n-butyl alcohol, the metal salt compound is palladium iodide, the amine is triethylamine employed in excess over the required quantities of said amine base, the oxidant salt is copper (I) iodide, and the amine salt compound is triethylammonium sulfate which is formed upon the addition of concentrated sulfuric acid.

* * * * *